(12) United States Patent
Kling et al.

(10) Patent No.: US 11,246,719 B2
(45) Date of Patent: Feb. 15, 2022

(54) MEDICAL REGISTRATION APPARATUS AND METHOD FOR REGISTERING AN AXIS

(71) Applicant: Brainlab AG, Munich (DE)

(72) Inventors: Sabine Kling, Unterschleißheim (DE); Luise Poitzsch, Au i. d. Hallertau (DE); Mario Schubert, Poing (DE); Melanie Stulpe, Munich (DE)

(73) Assignee: Brainlab AG, Munich (DE)

( * ) Notice: Subject to any disclaimer, the term of this patent is extended or adjusted under 35 U.S.C. 154(b) by 1031 days.

(21) Appl. No.: 14/907,106

(22) PCT Filed: Jan. 24, 2014

(86) PCT No.: PCT/EP2014/051398
§ 371 (c)(1),
(2) Date: Jan. 22, 2016

(87) PCT Pub. No.: WO2015/022084
PCT Pub. Date: Feb. 19, 2015

(65) Prior Publication Data
US 2016/0262913 A1    Sep. 15, 2016

(30) Foreign Application Priority Data

Aug. 13, 2013 (WO) ................. PCT/EP2013/066867
Aug. 14, 2013 (WO) ................. PCT/EP2013/067006
Dec. 12, 2013 (WO) ................. PCT/EP2013/076305

(51) Int. Cl.
*A61B 34/20* (2016.01)
*A61B 5/11* (2006.01)
(Continued)

(52) U.S. Cl.
CPC .......... *A61F 2/4657* (2013.01); *A61B 5/1114* (2013.01); *A61B 5/1127* (2013.01);
(Continued)

(58) Field of Classification Search
CPC .. A61F 2/4657; A61F 5/01; A61F 2002/4668; A61F 5/00; A61F 2/468;
(Continued)

(56) References Cited

U.S. PATENT DOCUMENTS 2,181,746 A * 11/1939 Siebrandt ........... A61B 17/8866
606/96
4,944,739 A *  7/1990 Torre ................. A61B 17/2812
606/207
(Continued)

FOREIGN PATENT DOCUMENTS

DE         4225112      12/1993
DE         10045376     4/2002
(Continued)

OTHER PUBLICATIONS

PCT/EP2014/051398 International Search Report dated Apr. 3, 2014.
(Continued)

*Primary Examiner* — Amanda Lauritzen Moher
*Assistant Examiner* — Amy J Shafqat
(74) *Attorney, Agent, or Firm* — Tucker Ellis, LLP

(57) ABSTRACT

The invention relates to a medical registration apparatus (1), comprising •two flanks (2a, 2b); •a pivot portion (3) around which at least one of the flanks (2a, 2b) is rotatable with respect to a rotation centre (3c, 3d) (FIG. 1, FIG. 3); •a contacting portion (4a, 4b) on each of the flanks (2a, 2b), each contacting portion (4a, 4b) being spaced apart from the rotation centre (3c, 3d); and •a sensor (5, 6) being arranged with an offset (r, FIG. 4 A) to a line (a) connecting the contacting portions (4a, 4b). The invention also relates to a data processing method for use with the medical registration apparatus.

14 Claims, 8 Drawing Sheets

(51) Int. Cl.
*A61B 34/10* (2016.01)
*A61B 90/00* (2016.01)
*A61B 5/00* (2006.01)
*A61F 2/46* (2006.01)
*A61F 5/01* (2006.01)
*A61B 17/00* (2006.01)

(52) U.S. Cl.
CPC ............ *A61B 5/6887* (2013.01); *A61B 34/10* (2016.02); *A61B 34/20* (2016.02); *A61B 90/06* (2016.02); *A61B 90/39* (2016.02); *A61B 2017/00951* (2013.01); *A61B 2034/105* (2016.02); *A61B 2034/2048* (2016.02); *A61B 2034/2055* (2016.02); *A61B 2034/2065* (2016.02); *A61B 2034/2068* (2016.02); *A61B 2090/067* (2016.02); *A61B 2090/363* (2016.02); *A61B 2090/3916* (2016.02); *A61B 2090/3937* (2016.02); *A61B 2090/3983* (2016.02); *A61B 2090/3991* (2016.02)

(58) Field of Classification Search
CPC .. A61F 2/4675; A61F 2002/4632; A61F 2/42; A61F 2/4202; A61F 2002/421; A61F 2002/4212; A61B 34/10; A61B 34/20; A61B 90/06; A61B 90/39; A61B 5/1114; A61B 5/1127; A61B 5/6887; A61B 2034/105; A61B 2034/2048; A61B 2034/2055; A61B 2034/2065; A61B 2034/2068; A61B 2090/067; A61B 2090/363; A61B 2090/3916; A61B 2090/3937; A61B 2090/3983; A61B 2090/3991; A61B 2017/00951; A61B 2034/2046; A61B 2034/2051; A61B 2034/207; A61B 2034/2072
See application file for complete search history.

(56) References Cited

U.S. PATENT DOCUMENTS

| | | | | |
|---|---|---|---|---|
| 5,147,365 A * | 9/1992 | Whitlock | ............. | A61B 17/158 606/88 |
| 5,797,919 A * | 8/1998 | Brinson | ............. | A61B 17/8866 606/105 |
| 6,159,217 A * | 12/2000 | Robie | ................. | A61B 17/155 606/207 |
| 6,491,700 B1 * | 12/2002 | Lavallee | ................ | A61B 90/11 606/130 |
| 6,551,316 B1 * | 4/2003 | Rinner | ............... | A61B 17/8866 606/205 |
| 8,298,139 B2 * | 10/2012 | Hamada | ............. | A61B 17/3439 600/233 |
| 8,323,295 B2 * | 12/2012 | Hufner | ................ | A61B 17/1757 606/105 |
| 8,475,470 B2 * | 7/2013 | von Jako | ............. | A61B 90/39 606/130 |
| 8,685,023 B2 * | 4/2014 | Dorawa | ............. | A61B 17/6466 606/59 |
| 8,699,090 B1 * | 4/2014 | Madhani | ............ | H04N 1/00307 358/1.15 |
| 8,728,087 B2 * | 5/2014 | Soliman | ............. | A61B 17/1767 606/88 |
| 8,821,501 B2 * | 9/2014 | Kecman | ............... | A61B 17/158 606/88 |
| 9,113,971 B2 * | 8/2015 | Metzger | ............... | A61B 17/809 |
| 9,339,319 B2 * | 5/2016 | Schmuck | ........... | A61B 17/8866 |
| 9,622,799 B2 * | 4/2017 | Orbay | ................ | A61B 17/8085 |
| 9,775,629 B1 * | 10/2017 | Henderson | ........... | A61B 17/151 |
| 10,463,434 B2 * | 11/2019 | Siegler | ................ | A61B 5/6847 |
| 2002/0161280 A1 * | 10/2002 | Chatenever | ........ | A61B 1/00045 600/112 |
| 2004/0106861 A1 | 6/2004 | Leitner | | |
| 2004/0181144 A1 | 9/2004 | Cinquin | | |
| 2004/0243148 A1 * | 12/2004 | Wasielewski | ....... | A61B 17/1707 606/130 |
| 2005/0234332 A1 | 10/2005 | Murphy | | |
| 2006/0200025 A1 | 9/2006 | Elliott | | |
| 2006/0282023 A1 * | 12/2006 | Leitner | ................. | A61B 5/103 600/595 |
| 2007/0162142 A1 * | 7/2007 | Stone | ..................... | A61B 34/20 623/20.14 |
| 2007/0244488 A1 * | 10/2007 | Metzger | ................ | A61B 90/36 606/90 |
| 2008/0071195 A1 | 3/2008 | Cuellar | | |
| 2009/0062869 A1 * | 3/2009 | Claverie | ................ | A61B 90/50 606/324 |
| 2009/0068620 A1 | 3/2009 | Knobel | | |
| 2009/0163930 A1 | 6/2009 | Aoude | | |
| 2010/0192961 A1 * | 8/2010 | Amiot | ..................... | A61G 13/12 128/882 |
| 2011/0071537 A1 * | 3/2011 | Koga | ................... | A61B 17/155 606/103 |
| 2011/0257657 A1 * | 10/2011 | Turner | ................. | A61B 17/175 606/103 |
| 2012/0029389 A1 | 2/2012 | Amiot | | |
| 2012/0053594 A1 * | 3/2012 | Pelletier | ................ | A61B 34/20 606/102 |
| 2012/0065496 A1 * | 3/2012 | Stratton | ........... | G01R 33/34046 600/414 |
| 2012/0143049 A1 | 6/2012 | Kneubauer | | |
| 2012/0157887 A1 * | 6/2012 | Fanson | ..................... | A61F 2/46 600/595 |
| 2012/0221059 A1 * | 8/2012 | Mollman | ........... | A61B 17/7074 606/277 |
| 2013/0041289 A1 * | 2/2013 | Sena | ......................... | A61B 5/11 600/595 |
| 2014/0207192 A1 * | 7/2014 | Gordon | .............. | A61B 17/7068 606/249 |

FOREIGN PATENT DOCUMENTS

| | | | | |
|---|---|---|---|---|
| DE | 10045376 A1 * | 4/2002 | ........... | A61B 5/4528 |
| WO | 9500075 | 1/1995 | | |
| WO | 0048507 | 8/2000 | | |
| WO | 2006131373 | 12/2006 | | |
| WO | 2009059434 | 5/2009 | | |
| WO | 2011012169 | 2/2011 | | |
| WO | 2011020505 | 2/2011 | | |
| WO | 2013052187 | 4/2013 | | |
| WO | 20130053398 | 4/2013 | | |

OTHER PUBLICATIONS

PCT/EP2013/066867 International Search Report dated Apr. 7, 2014.
PCT/EP2013/067006 International Search Report dated Apr. 11, 2014.
PCT/EP2013/076305 International Search Report dated Apr. 4, 2014.

* cited by examiner

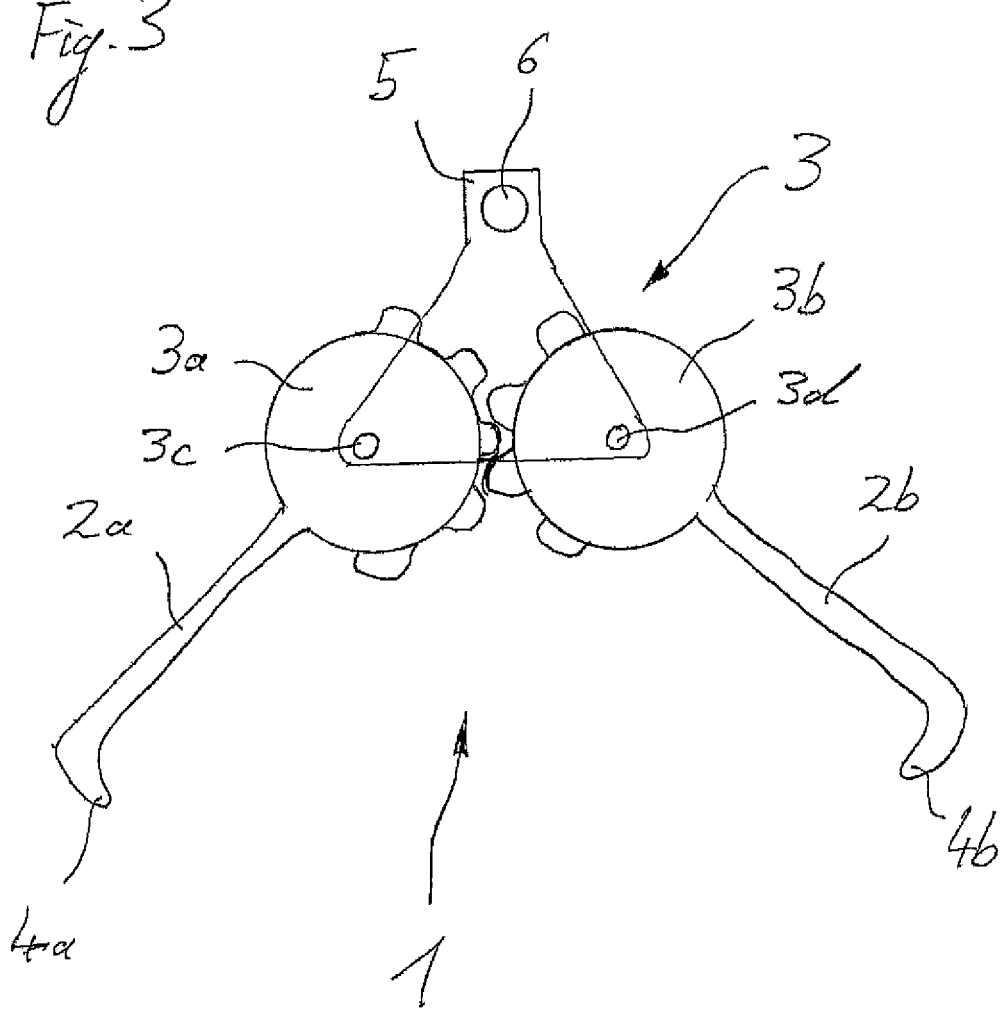

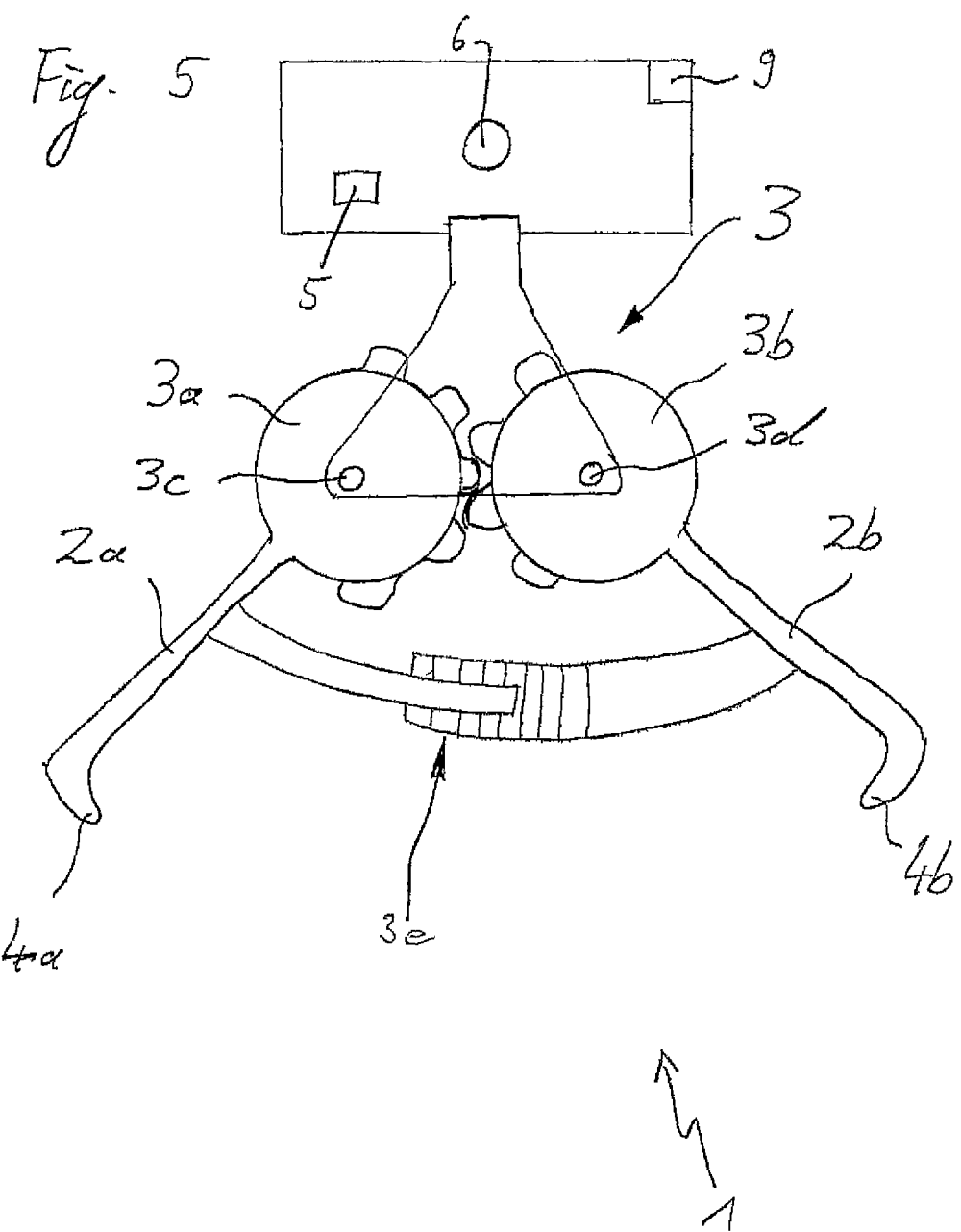

MEDICAL REGISTRATION APPARATUS AND METHOD FOR REGISTERING AN AXIS

RELATED APPLICATION DATA

This application is a national phase application of International Application No. PCT/EP2014/051398 filed Jan. 24, 2014, published in the English language, which claims priority to International Application No. PCT/EP2013/066867 filed on Aug. 13, 2013, International Application No. PCT/EP2013/067006 filed on Aug. 14, 2013, and International Application No. PCT/EP2013/076305 filed on Dec. 12, 2013, which are hereby incorporated herein by reference.

The present invention relates to a medical registration apparatus which allows registration of an axis of in particular an anatomical body part and a medical data processing method for evaluating the results of using the registration apparatus.

When planning orthopaedic surgical procedures such as a total endoprosthesis (TEP) of the knee or the hip joint, it is often desirable to have knowledge of the position of a specific axis in the patient's body which characterises the geometry of the anatomical body part which is subject to the procedure. For example, a TEP of the knee generally requires knowledge of the position and orientation of the mechanical axis of the femur on the respective leg of the patient. The mechanical axis of the femur is in general defined by its proximal and distal end points. In particular, the mechanical axis of the femur need not be identical to the anatomical (longitudinal) femur axis. The proximal end point is the centre of rotation of the femoral head. The distal end point is commonly determined as approximately the centre between the medial and lateral epicondylus. It is in general assumed that the distal end point of the femur axis lies on a straight line connecting the medial and lateral epicondyles. For determining the position of the distal end point of the mechanical femur axis, it is thus desirable to determine the position (and preferably also orientation) of the straight line connecting the medial and lateral epicondyles in a coordinate system in which the respective surgical procedure is planned.

Known approaches to determining the position of the mechanical axis of the femur involve using a pointer to inform a navigation system about the position of in a general at least two landmarks on the femur (namely, the positions of the proximal endpoint and of the distal end point of the mechanical femur axis). This approach is, however, quite cumbersome, involves a potential lack of precision and requires the pointer to be visible for a detection unit of the navigation system throughout the whole procedure of acquiring the information about the position of the landmarks.

Similar issues arise when using a known approach for determining the position and orientation of a characteristic axis of the pelvis for hip total endoprosthesis procedures. Such known approaches also involve using a pointer to inform a navigation system about the positions of characteristic landmarks on the pelvis, such as two out of a point on the anterior superior iliac spine, a point at the anterior acetabular rim and a point on the midsagittal plane of the patient. This approach is associated with similar shortcomings as the aforementioned approach for planning knee total endoprosthesis.

A problem to be solved by the invention thus is to provide an apparatus and corresponding method for improved, in particular more efficient, precise and flexible, determination of the position of an axis which in particular characterises an anatomical body part.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature. A feature of one embodiment which adds an additional function to another embodiment can in particular be added to said other embodiment.

EXEMPLARY SHORT DESCRIPTION OF THE INVENTION

In the following, a short description of specific features of the present invention is given which shall not be understood to limit the invention only to the features and combinations of features described in this section.

The invention relates to a medical registration apparatus having at least one of an optical sensor and an inertial sensor, and contacting portions which can be placed in a predetermined (in particular) known spatial relationship relative to landmarks on an anatomical body part (such as the knee or the pelvis) which is to be analysed. Based on rotating the registration apparatus in this position and data gathered by the at least one sensor (preferably, the sensor is an inertial sensor) which describes the rotational movement, the position, in particular the orientation, of an axis characterising the anatomical body part in a coordinate system used to plan an envisaged medical procedure can be determined.

The invention also relates to a data processing method for use with the registration apparatus which aims at determining the position and preferably the orientation, of the axis in the mentioned coordinate system. The validity of this method is based in particular on the idealising assumption that the proximal end point of the mechanical tibia axis is identical to the distal end point of the mechanical femur axis. The position of the distal end point of the mechanical femur axis is determined using the aforementioned apparatus (in particular by placing it on the patient's skin above the femoral epicondyles and registering it relative to an external reference placed on patient's skin above the malleoli while the leg is being held in extension). All other measurements are also taken with the leg in extension.

Furthermore, the invention is directed to a corresponding computer program, computer configured to execute such a program and a medical navigation system comprising in particular that computer.

GENERAL DESCRIPTION OF THE INVENTION

In this section, a description of the general, in particular preferred, features of the present invention is given.

A first aspect of the present invention relates to a medical registration apparatus. Within the framework of this disclosure, registration and method steps of registering encompass determining the spatial location of at least one specific point of an actual (physical) object within a space, in particular relative to a reference system (coordinate system), and preferably notifying information about that spatial location (i.e. position, such as values of coordinates defining that position) to a navigation system. For example, the actual object is an anatomical body part such as a knee joint or a pelvis, comprising a plurality of points which define for example landmarks, and the positions of those points in a coordinate system which is used to plan a medical procedure shall be determined and notified to the navigation system.

The inventive medical registration apparatus is an apparatus which is usable in conjunction with a method of registering an anatomical body part, wherein corresponding methods, in particular data processing methods, are also disclosed in this document and also form a part of the present invention. In particular, the inventive registration apparatus supports registration of an anatomical body part, in particular of landmarks on the anatomical body part.

The medical registration apparatus preferably has at least two flanks (in particular exactly two flanks). Preferably, these two flanks together form the shape of a forceps, wherein the flanks can be of linear or curved shape along at least part of their length. Furthermore, the flanks are preferably arranged relative to one another in a symmetrical manner, in particular they fulfil a condition of mirror plane symmetry relative to each other.

Preferably, the registration apparatus comprises a pivot portion around which at least one of the flanks is rotatable with respect to a rotation centre. Further preferably, the pivot portion is at least substantially partly located in the mirror plane of symmetry. According to a specific preferred embodiment, the pivot portion comprises a joint element, in particular a hinge element such as a transmission, in particular a gearing, which allows to rotate the at least one of the flanks with respect to the rotation centre. According to a further preferred embodiment, at least two of the flanks are rotatable with respect to the rotation centre. In particular, the pivot portion is at least partly arranged in the rotation centre. According to a further preferred embodiment, different rotation centres are provided so that each flank can rotate about its own rotation centre. For example, two different rotation centres are provided in the case of the registration apparatus comprising exactly two flanks, each flank having its own rotation centre. For example, each one of the flanks constitutes a rotary wing, and the flanks interact with each other by means of gear wheels, wherein preferably one gear wheel is attached to the end (in particular proximal end) of each one of the flanks. Each one of the gear wheels then preferably has its own rotation centre and is rotatably attached to the pivot portion. According to one embodiment, there are no further gear wheels apart from those which are attached to the flanks, i.e. the gear wheels and flanks, respectively, interact directly with each other. According to another, different, embodiment, there are further, in particular two further, interacting gear wheels positioned in between the gear wheels to which the flanks are attached in order to allow for example for smaller dimensioning of the gear wheels.

Due to the gear wheels, a movement of one of the flanks leads to corresponding movement of the other one (in the other sense of rotation) of the flanks by rotary engagement of the respective gear wheels. According to an even further embodiment, at least one of the two flanks is arranged so as to be rotatable around a rotational axis which is fastened to the pivot portion. In such an embodiment, at least one other one of the flanks has a fixed position relative to the rotational axis. In both of the aforementioned embodiments, i.e. the embodiment having gear wheels attached to the flanks and the embodiments having the rotational axis on which at least one of the flanks is hinged, a biasing means (such as for example a spring—in particular a coil spring) may be located between the flanks and attached to each one flank at each one of its ends so as to bias the flanks towards each other, in particular to keep the flanks at a minimal opening angle (in particular, to bias the flanks into a closed position) especially at least as long as no counter force acts on the biasing means. Also, in both of the aforementioned embodiments, the registration apparatus preferably comprises a locking mechanism (e.g. at least one of a ratchet, interlocking teeth and a tension spring) to secure the flanks in a fixed position with respect to each other. For example, the locking mechanism is located in between the flanks and preferably fastened to each one of the flanks. A combination of the interlocking mechanism with one of the aforementioned joints (i.e. the simple rotational axis and the gear wheel configuration described above) which allow rotation of the flanks relative to each other supports single-handed operation of the registration apparatus. In particular, the flanks may initially be disposed in a completely open position (as far as the interlocking mechanism, for example, in the case of a ratchet allows) and only one hand will be needed to close the flanks which will be kept in the respectively selected closed state by the interlocking mechanism.

Preferably, a contacting portion is disposed on each one of the flanks in particular at the distal end of the flank (i.e. at the end which is opposite to the end of the flank which is positioned towards the pivot portion). The contacting portion is preferably configured, in particular shaped, to contact an anatomical body part. In particular for the above-mentioned application in knee surgery (in the following also called "knee application"), the contacting portion preferably is at least substantially disc-shaped or cup-shaped so as to fit onto the lateral and medial malleolus of a knee. In particular for the above-mentioned application on the pelvis (in the following also called "pelvis application"), the contacting portion takes the form of a pointed end (such as the shape of an arrow head) which supports precise positioning of the distal ends of the flanks on respective landmarks. A cup-shaped contacting portion is connected to the respective flank preferably via a joint mechanism, in particular a rotation mechanism, which enables rotation about an axis through the distal end of the flank and through the contacting portion. This allows for a rotational movement of the registration apparatus, in particular of the flank, around the axis while the contacting portion is held in position on the respective landmark. In particular, this rotational movement occurs parallel to, in particular in, the aforementioned mirror plane of symmetry. Furthermore, each contacting portion is preferably spaced apart from the rotations centre around which at least one of the flanks is rotatable. Preferably, the distal end of a flank points towards its associated contacting portion, and its proximal end points towards the rotation centre.

Preferably, the registration apparatus comprises a sensor which is arranged for example with an offset (which is in particular greater than zero) to a line (in particular a straight line) connecting the contacting portions. In particular, the sensor is at least one of an inertial sensor (for example a digital gyroscope) and an optical sensor (for example, a digital camera) which is configured to acquire signals which comprise information about the current spatial relationship of the registration apparatus (in particular of the sensor) relative to at least one of a global coordinate system and a reference such as an optical reference (for example, reference marker device having a marker comprising a graphical pattern which is detectable in the visible wavelength range, for example by analysis of a digital image of the marker) which may be attached for example to a patient's ankle (for example on the leg on which the registration apparatus is to be used in particular in the case of the aforementioned knee application). Within the framework of this disclosure, the term of spatial relationship encompasses at least one of position and orientation.

Preferably, the sensor is disposed at or close to the proximal ends of the flanks and configured to transmit data (for example via a wireless connection provided by a wireless communication interface contained in the registration apparatus) containing information indicating the position of the sensor to the computer of a navigation system which is used to plan the envisaged medical procedure. Such information is for example at least one of a) inertial navigation information which allows to determine the spatial relationship of the inertial sensor relative to a predetermined, in particular known, reference position and b) image information allowing to determine the spatial relationship of the optical sensor relative to an imaged entity, for example an external optical reference—in particular marker—preferably having a predetermined, in particular known, position in a coordinate system used for planning the envisaged medical procedure (also called "global coordinate system").

According to a specific embodiment, the sensor comprises both an optical sensor and an inertial sensor, and the optical sensor has a predetermined (in particular known, preferably also fixed) spatial relationship relative to the inertial sensor. This allows to for example simultaneously determine the spatial relationship of the sensor relative to the aforementioned optical reference and relative to the global coordinate system in which the envisaged medical procedure is planned. This supports in particular ensuring the desired orientation of the sensor relative to the optical reference while at the same time being able to measure the position and preferably the orientation of an axis connecting the landmarks in the global coordinate system. Having a predetermined (in particular known) spatial relationship of the optical sensor relative to the inertial sensor also allows to determine the position of the optical reference in a global coordinate system based on image data describing the optical reference which is captured by the optical sensor. Alternatively, the position of the optical reference in the global coordinate system is predetermined, and the position of the optical sensor relative to the optical reference is determined based on predetermined (in particular known) information about the image appearance of the optical reference at standard imaging conditions and analysis of a digital image taken of the optical reference by the optical sensor. Based on a known standard appearance of the optical reference in such an image at predetermined (in particular known) imaging conditions, the image information describing an image of the optical reference can be transformed into coordinates of the optical reference and the global coordinate system based on the positional measurements (in particular movement measurements) of the inertial sensor.

Preferably, the flanks are shaped and attached to the pivot portions so that the contacting portions on each of the flanks and a rotation centre (all the rotation centres, respectively) lie in the same plane for every opening angle of the flanks. In a forceps-shaped configuration of the disclosed registration apparatus, the flanks thus preferably take the position of the forceps flanks which describe a specific opening angle in each position of the flanks relative to each other. The plane in which that angle lies is preferably fixed and the same for any opening angle of the flanks.

Preferably, the registration apparatus is at least substantially symmetrical relative to a mirror plane which describes a mirror symmetry between in particular the positions of the contacting portions. Preferably, at least the detection part of the sensor (in the case of an inertial sensor, for example a gyroscope; in the case of an optical sensor, for example an entry lens and/or an imaging chip) are disposed on the mirror plane. In particular, the respective part of the sensor is positioned on the mirror plane of symmetry for every opening angle of the flanks or has a predetermined (in particular known) spatial relationship relative to the mirror plane. Preferably, the pivot portion (in particular a hinge element contained in the pivot portion), more particularly the rotation centre, is also located on the mirror plane for every opening angle of the flanks. Further preferably, each contacting portion has the same distance from its respective rotations centre, and the flanks are therefore preferably also symmetric relative to the mirror plane.

In a second aspect, the invention relates to a method, in particular a data processing method (more precisely, a medical data processing method) for registering, with respect to a sensor, an axis of the above-described registration apparatus. The sensor is in particular the above-described sensor of the registration apparatus. The axis of the registration apparatus is preferably an axis defined by a line (in particular a straight line) connecting the contacting portions of the registration apparatus. Since the contacting portions are designed to designate the positions of respective landmarks (preferably, they are configured to contact an in particular exterior body surface having preferably a known spatial relationship relative to the landmarks—which does not require any surgical activity to be carried out for performing the disclosed method), the axis of the registration apparatus is equal to in particular the above-described axis of the anatomical body part, the position of which is to be determined using the disclosed registration apparatus, and therefore in particular also by performing the disclosed method.

It is assumed that, before execution of the data processing method for registering the axis with respect to the sensor, the disclosed registration apparatus has been positioned relative to the landmarks such that the positions of the contacting portions define the axis connecting the landmarks (i.e. the axis characterising the anatomical body part). In particular, the contacting portions have been positioned on the outer body surface of the patient, in the case of the knee application for example such that the disc- or cup-shaped contacting portions are in stable contact with the skin above the medial and lateral condyles, respectively. The registration apparatus, in particular the flanks and the sensor, are then rotated around the axis.

Preferably, sensor movement data representing the rotational movement of the sensor around the axis is then preferably acquired. If the sensor comprises an optical sensor as described above, and the medical procedure to be planned is the above-described knee application, preferably an optical reference is attached to the ankle of the respective patient's leg within advantageously predetermined (in particular known) spatial relationship relative to the medial and lateral malleolus. The optical reference preferably is a marker of the type having a predetermined (in particular known) and graphical pattern for detection by the optical sensor. Based on the image information describing the image appearance of the optical reference which is captured by the optical sensor, the sensor movement data comprising information describing the rotational movement of the sensor in particular in a direction (rotational plane) perpendicular to the axis can be determined by applying known data processing methods for image analysis. In particular, the position of the plane in which the sensor is rotated in the global coordinate system can be determined based on the predetermined (in particular known) position of the optical reference in the global reference and the image information describing the image appearance of the optical reference. If the sensor comprises an inertial sensor, the sensor movement data can alternatively or additionally be acquired from the inertial information generated by the inertial sensor during the rotational movement.

Based on the sensor movement data, preferably axis registration data is determined. The axis registration data represents in particular the spatial relationship of the axis relative to the sensor, more particularly at least one of a distance between the axis and the sensor (in particular from the axis to the sensor) and the orientation between the axis and the sensor. In particular, the spatial relationship between the axis connecting the contacting portions and the sensor does not need to be known. Rather, the position of the axis is determined on the basis of at least one of the image information describing the optical reference and the information about the movement of the sensor. The information about the movement of the sensor can alternatively or additionally be gathered by an inertial sensor, if the sensor includes an inertial sensor. For example, the positions on the curved trajectory on which the sensor is rotated and at which detection of the optical reference starts and finishes, respectively, are acquired by the disclosed method and serve determine the centre around which the sensor is rotated since they define a section of a circle within which the sensor is rotated. The plane in which the sensor is rotated and the determined centre of rotation of the sensor serve to determine the axis since it is known that the axis runs perpendicular to the plane of rotation. In order to determine the position and preferably also orientation of the axis in the global coordinate system, the sensor is preferably navigated, i.e. its position in the global coordinate system during the rotational movement is preferably known. This may be achieved by attaching a marker to the sensor and detecting the position of that marker with a detection unit of the navigation system or by determining the position of the sensor relative to the optical reference if the position of the optical reference in the global coordinate system is known, for example by detecting it separately with the detection unit of the navigation system. Alternatively or additionally, and if the sensor comprises an inertial sensor, navigation of the sensor by acquiring inertial information acquired from the inertial sensor which describes a movement of the inertial sensor relative to a known position in for example the global coordinate system may be used to determine the position of the sensor.

In addition, the above-described data processing method can also be used for registering the axis relative to an external reference, which is in particular the above-mentioned optical reference. In this case, the above-described steps of the data processing method for registering the axis of the registration apparatus relative to the sensor, the following steps are then preferably performed.

Optical sensor data is acquired which represents in particular the distance between the optical sensor of the registration apparatus and the external reference. The information about the distance is acquired by analysis of the image representation of the external reference acquired by the optical sensor as described above. Based on the axis registration data and the optical sensor data, preferably spatial axis data representing the spatial relationship of the axis relative to the external reference is then determined as described above. In this embodiment, it is advantageous that the spatial relationship of the inertial sensor relative to the optical sensor is predetermined (in particular known and advantageously fixed).

In the above-described knee application, the data processing method is also suitable for determining the position of the proximal end point of the longitudinal (i.e. the proximodistal) tibia axis relative to an external reference under the aforementioned assumption that the proximal end point of the tibia axis is identical to the distal end point of the mechanical femur axis. To this end, preferably proximal landmark position data is acquired which describes the position of the proximal landmarks, i.e. of the epicondyle which define the position of the distal end point of the mechanical femur axis. According to a less preferred embodiment, also distal landmark position data is acquired which describes, in particular represents the spatial relationship of the distal end point of the mechanical femur axis relative to the external reference (and preferably also relative to the sensor) is determined. The proximal landmark position data is determined for example based on signals emitted from the inertial sensor which indicate the inertial information, in particular based on the information about the position of the inertial sensor which can be generated based on the inertial information. Based on for example the inertial information, the position and preferably also orientation of the axis connecting the femoral epicondyle can then be determined without using an optical sensor. Alternatively or additionally, the proximal landmark position data can be acquired based on determining the position of the optical sensor by detecting the external reference with the optical sensor (and thus determining the position of the optical sensor relative to the external reference) and also detecting the position of the external reference with an optical detection unit of a navigation system and thereby determining the position of the external reference in the global coordinate system. The sensor in both cases has a defined spatial relationship relative to the proximal landmarks so that in both cases the positions of the landmarks in the global coordinate system can be determined via the sensor measurements. [Hier sollten aus patentrechtlichen Gründen zwei verschiedene Varianten beschrieben werden, auch wenn Brainlab die letztere vermutlich nicht verwirklicht.]

The distal landmark position data represents in particular the position of two distal landmarks of the tibia relative to the sensor. The distal landmarks preferably are the medial and lateral malleolus of the ankle joint on the leg of which the knee being analysed is part. The distal landmark position data is determined preferably based on (in particular by) detecting the aforementioned external reference. The external reference is detected with the (optical) sensor which has been brought into a defined spatial relationship relative to the positions of the proximal landmarks, i.e. relative to the epicondyli of the femur, preferably while the respective leg is an extended state (in order to minimize errors). In particular, the external reference is the above-described optical reference which is attached to the ankle joint in a manner that ensures the predetermined spatial relationship of the optical reference relative to the medial and lateral malleolus.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, in particular electrical, in particular technically generated) signal wave, in particular a digital signal wave, carrying information which represents the program, in particular the aforementioned program, which in particular comprises code means which are adapted to perform any or all of the method steps described herein.

Furthermore, the invention relates to a medical navigation system comprising a detection unit for detecting the position of the above-described registration apparatus, and the aforementioned computer. The detection unit can be for example a stereoscopic camera for detecting a marker device attached to the registration apparatus with a predetermined (in particular known and advantageously fixed) spatial relationship relative to the registration apparatus. Alternatively or additionally, the detection unit can be for example the optical sensor of the registration apparatus which detects information describing the position of the registration apparatus relative to the optical reference, the position of which in the global coordinate system is known to the computer of the navigation system. The data acquired by the optical sensor is transmitted to the computer preferably by a wireless communication interface included in the registration apparatus.

DEFINITIONS

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a technical and in particular tangible device.

It is the function of a marker to be detected by a marker detection device (for example, a camera or an ultrasound receiver or analytical devices such as CT or MRI) in such a way that its spatial position (i.e. its spatial location and/or alignment) can be ascertained. The detection device is in particular part of a navigation system. The markers can be active markers. An active marker can for example emit electromagnetic radiation and/or waves which can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape. A marker can also be a marker which is detectable by optical means which operate in the visible wavelength range. Such a marker displays for example a graphical pattern which can be present (e.g. stuck with a label, printed, painted or engraved) on one of its surfaces. That pattern is predetermined and in particular known to the inventive method and therefore allows to determine the spatial relationship between the marker and an optical detection unit (e.g. a common digital camera which advantageously provides the required resolution to detect an evaluate the image information representing the graphical pattern) in particular by data analysis of the appearance of the marker in an image (in particular a digital image) taken with the optical detection unit.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is in particular known to a navigation system and is for example stored in a computer of the navigation system.

A pointer is a rod which comprises one or more—advantageously, two—markers fastened to it and which can be used to measure off individual co-ordinates, in particular spatial co-ordinates (i.e. three-dimensional co-ordinates), on a part of the body within the framework of a morphing method, wherein a user guides the pointer (in particular, a part of the pointer which has a defined and advantageously fixed position with respect to the at least one marker attached to the pointer) to the position corresponding to the coordinates, such that the position of the pointer can be determined by using a surgical navigation system to detect the marker on the pointer. The relative location between the markers of the pointer and the part of the pointer used to measure off co-ordinates (in particular, the tip of the pointer) is in particular known. The surgical navigation system then enables the location (of the three-dimensional co-ordinates) to be assigned to a predetermined body structure, wherein the assignment can be made automatically or by user intervention.

The present invention is also directed to a navigation system for computer-assisted surgery. This navigation system preferably comprises the aforementioned computer for processing the data provided in accordance with the data processing method as described in any one of the preceding embodiments. The navigation system also preferably comprises a user interface for receiving the calculation results from the computer. The user interface provides the received data to the user as information. Examples of a user interface include a display device such as a monitor, or a loudspeaker. The user interface can use any kind of indication signal (for example a visual signal, an audio signal and/or a vibration signal). An example of a display device is an augmented reality device (also called augmented reality glasses) which may be used as goggles for navigating. A specific example of such augmented reality glasses is Google Glass (trademark of Google Inc.). An augmented reality device may be used to both input information into the computer of the navigation system by user interaction and to display information outputted by that computer.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In particular, the invention does not involve or in particular comprise or encompass an invasive step which would represent a substantial physical interference with the body requiring professional medical expertise to be carried out and entailing a substantial health risk even when carried out with the required professional care and expertise. In particular, the invention does not comprise a step of positioning a medical implant in order to fasten it to an anatomical structure or a step of fastening the medical implant to the anatomical structure or a step of preparing the anatomical structure for being fastened to the medical implant. More particularly, the invention does not involve or in particular comprise or encompass any surgical or therapeutic activity. The invention is instead directed in particular to positioning the tool relative to the medical implant, which may be outside the patient's body. For this reason alone, no surgical or therapeutic activity and in particular no surgical or therapeutic step is necessitated or implied by carrying out the invention.

DESCRIPTION OF THE FIGURES

In the following, exemplary embodiments of the invention will be described by reference to the figures, wherein the invention shall not be limited to the features described in connection with the figures, and wherein

FIG. 3 shows a pivoting portion and two flanks having pointed contacting portions as well as a pivot portion comprising a gear mechanism for a configuration of the inventive registration apparatus according to a second embodiment;

FIG. 5 shows a setup of the inventive registration apparatus according to a third embodiment;

FIG. 1 shows the setup for the knee application in which the inventive registration apparatus 1 having an inertial sensor 5 and an optical sensor 6 and comprising two flanks 2a, 2b having contacting portions 4a, 4b (the latter one not being shown in FIG. 1) at their distal ends is placed on the skin surface of a knee 11. The contacting portions 4a, 4b are placed on the knee such that they lie on the outer body surface (in particular on the skin on the patient) above the medial and lateral condyles, respectively. The registration apparatus 1 also comprises an interlocking mechanism 3e for fixing the flanks 2a, 2b in their position relative to each other. If not fixed by the interlocking mechanism 3e, the flanks are freely rotatable around a rotation centre 3c in the pivot portion 3.

Figure 1:
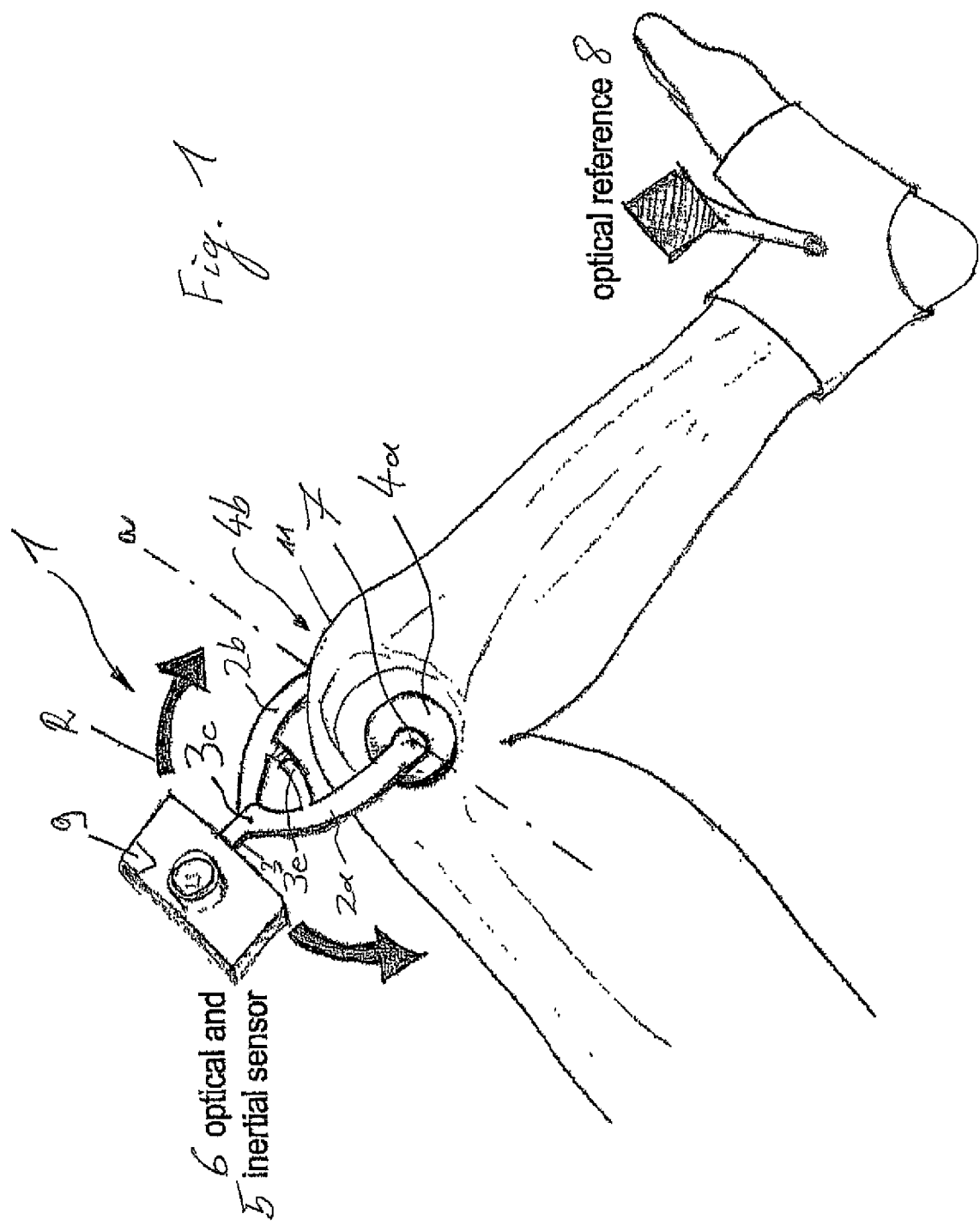
FIG. 1 shows a configuration of the inventive registration apparatus for the knee application according to a first embodiment.

The registration apparatus 1 is placed on the anatomical body part embodied by for example the knee 11 and rotated in the direction of rotation R. The trajectory associated with the rotation R lies in a plane which is perpendicular to the axis a connecting the contacting portions 4a, 4b and which is assumed to be identical with the characteristic axis of the anatomical body part (the knee 11) which connects the two landmarks, namely the medial and lateral epicondyles. During this rotation, the contacting portions 4a, 4b are not rotated since they are connected to the flanks 2a, 2b via a rotation mechanism 7 which allows the flanks 2a, 2b and the contacting portions 4a, 4b to freely rotate relative to each other. Furthermore, an optical reference 8 is placed on the ankle of the associated leg, for example by means of a shoe which fits over the patient's foot. The shoe and the optical reference 8 are constituted such that the spatial relationship between the position of the optical reference 8 and the positions of the medial and lateral malleolus of the ankle is known. Therefore, the optical reference 8 can be said to represent the positions of the malleoli. Furthermore, the optical reference 8 is attached to the shoe preferably such that it represents the position of the distal end point of the longitudinal tibia axis, which is approximately the centre between the medial and lateral malleolus (in particular, the position of the distal end point divides the distance between the two malleoli in a predetermined, in particular known, ratio). The number and type of positions determined by the optical sensor during its rotation are not predetermined. It would essentially be sufficient to acquire two positions during the rotation in order to gather the required geometric information. According to one more specific embodiment, the positions can be acquired in the following manner: During rotation of the optical and inertial sensor 5, 6 along the direction R, the positions along the trajectory of rotation at which the optical sensor starts detecting the optical reference 8 and at which it stops detecting the optical reference 8 (since the optical reference 8 enters and leaves, respectively, field of view of the optical sensor 6) are acquired. Based on these positions, a curved (rotational) trajectory representing a section of a circle is defined and used to determine the centre of rotation on which the axis a lies. Alternatively or additionally, the optical sensor 6 is used only to determine the distance between the optical sensor 6 and the optical reference 8, and the inertial sensor 5 is used to determine information about the rotational movement of the registration apparatus 1 in the direction R. This information is then contained in particular in the above-described sensor movement data. The distance between the optical sensor 6 and the optical reference 8 is contained in particular in the above-described optical sensor data. Based on the sensor movement data, the above-described axis registration data representing the spatial relationship of the axis a relative to the sensor 5, 6 is then determined. Even further, spatial axis data representing the spatial relationship of the axis a relative to the optical reference 8 can also be determined based on the optical sensor data and the axis registration data.

If the sensor comprises (in particular only) an inertial sensor, the aforementioned information acquired by optical detection may be acquired (in particular only) from the inertial information acquired by the inertial sensor.

Figure 2:
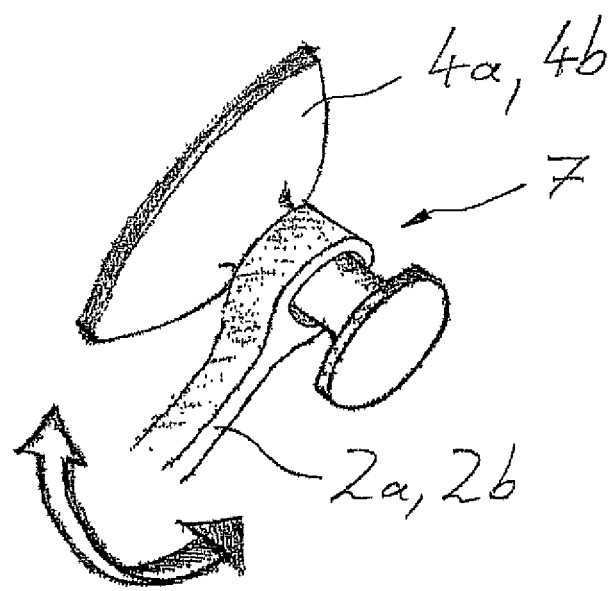
FIG. 2 shows a cup-shaped configuration of a contacting portion.

FIG. 2 contains an illustration of the rotation mechanism 7 for a cup-shaped contacting portion 4a, 4b, by which it is attached to a flank 2a, 2b. In particular, the cup-shaped contacting portion 4a, 4b comprises a rotational axis which is led through a through hole at the distal end of the flank 2a, 2b and at its end pointing away from the cup of the cup-shaped contacting portion 4a, 4b comprises a knob which secures it to the flank 2a, 2b while keeping the cup-shaped contacting portion 4a, 4b rotatable relative to the flank 2a, 2b.

FIG. 3 is an illustration of a medical registration apparatus 1 according to a second embodiment in which the pivoting portion 3 contains two rotation centres 3c, 3d around which each one gear wheel 3a, 3b is able to rotate. The gear wheels 3a, 3b are arranged and constituted to engage into each other and are (in particular fixedly) attached to each one flank 2a, 2b. Each one of the flanks 2a, 2b has at its distal end a point-like contacting portion 4a, 4b. Rotational movement of one of the flanks 4a, 4b causes the other one of the flanks to be moved by the same amount in the other rotational direction by interaction of the gear wheels 3a, 3b. In particular, the flanks 2a, 2b always have positions which are symmetric relative to a mirror plane of symmetry which—in the illustration of FIG. 3—runs perpendicular to the plane of projection. In the configuration of FIG. 3, also the rotation centres 3c, 3d have positions which are symmetric relative to that mirror plane.

Figure 4A:
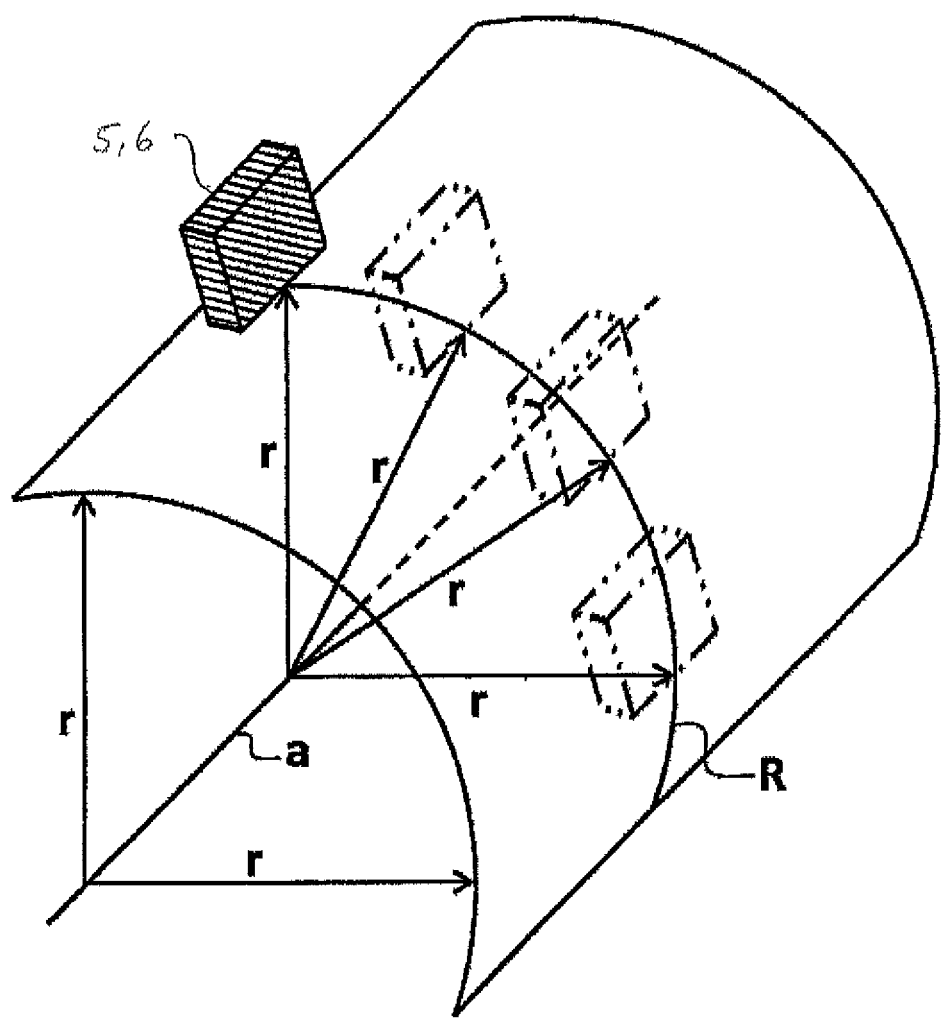
FIG. 4A shows the movement path of the registration apparatus during rotation around the axis of the anatomical body part.

FIG. 4A shows the geometric quantities which are used to determine a distance between the optical and inertial sensors 5, 6 and the axis a during rotational movement along the trajectory R. Measurements conducted by the inertial sensor 5 allow to determine the curvature of the trajectory R, and based on these measurements, the distance R of this curved trajectory R from the respective centre of rotation through which also the axis a runs perpendicular to the plane in which the trajectory R lies is determined.

Figure 4B:
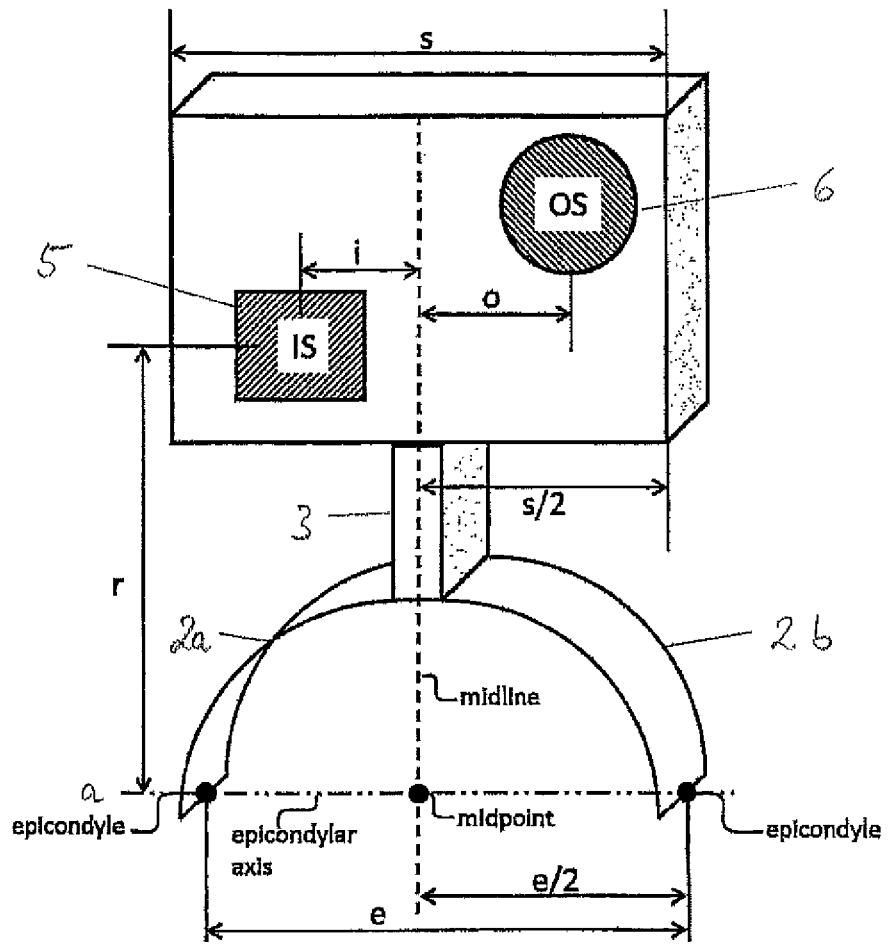
FIG. 4B shows a general geometry of the registration apparatus.

FIG. 4B illustrates the geometric quantities which are preferably used to determine the distance of the inertial sensor 5 (also abbreviated as "IS") and/or the optical sensor 6 (also abbreviated as "OS") from the axis a which connects the contacting portions 4a, 4b and the medial and lateral epicondylus, respectively. This axis is also called epicondylar axis. The distance r of the inertial sensor 5 from the axis a is preferably determined by the method described in particular with relation to FIG. 4A. The midpoint representing the centre of rotation along the trajectory R has a known distance from each epicondylus of e/2, where e is the distance between the contacting portions 4a, 4b. The distance r of the inertial sensor 5 from the epicondylar axis a is used to determine the midpoint in consideration of the known distance i of the inertial sensor 5 from the mirror plane of symmetry and the distance o of the optical sensor 6 to the mirror plane of symmetry. Dimension s denotes the lateral extension of the housing comprising the inertial sensor 5 and the optical sensor 6, wherein the pivoting portion 3 is disposed at s/2 along the lateral extension of the housing. The flanks 2a, 2b are disposed on the lower end of the pivoting portion 3 in a manner which is symmetric relative to the mirror plane of symmetry.

FIG. 5 shows the registration apparatus 1 according to a third embodiment which is suitable for conducting in particular the above-described knee application. The configuration of FIG. 5 is based on the configuration of FIG. 3, wherein the same reference signs denote the same features. In addition to FIG. 3, the embodiment of FIG. 5 comprises a separate housing for the inertial sensor 5 and the optical sensor 6 which is attached to the upper end of the pivoting portion 3 and also comprises a communication interface 9 such as an antenna for wireless data transmission to a navigation system which comprises a computer configured to execute the data processing method for registering the axis a as described above. Furthermore, the registration apparatus 1 according to FIG. 5 comprises an interlocking mechanism 3e embodied by a ratchet, wherein the two fixed ends of the ratchet are attached to each one flank 2a, 2b. The ratchet is preferably configured such that, if the flanks 4a, 4b are closed, i.e. the opening angle between the flanks 4a, 4b on the interior (i.e. in the inside of the flanks pointing towards the interlocking mechanism 3e) is decreased, the ratchet locks the flanks 2a, 2b such that the opening angle cannot be increased again.

Figure 6:
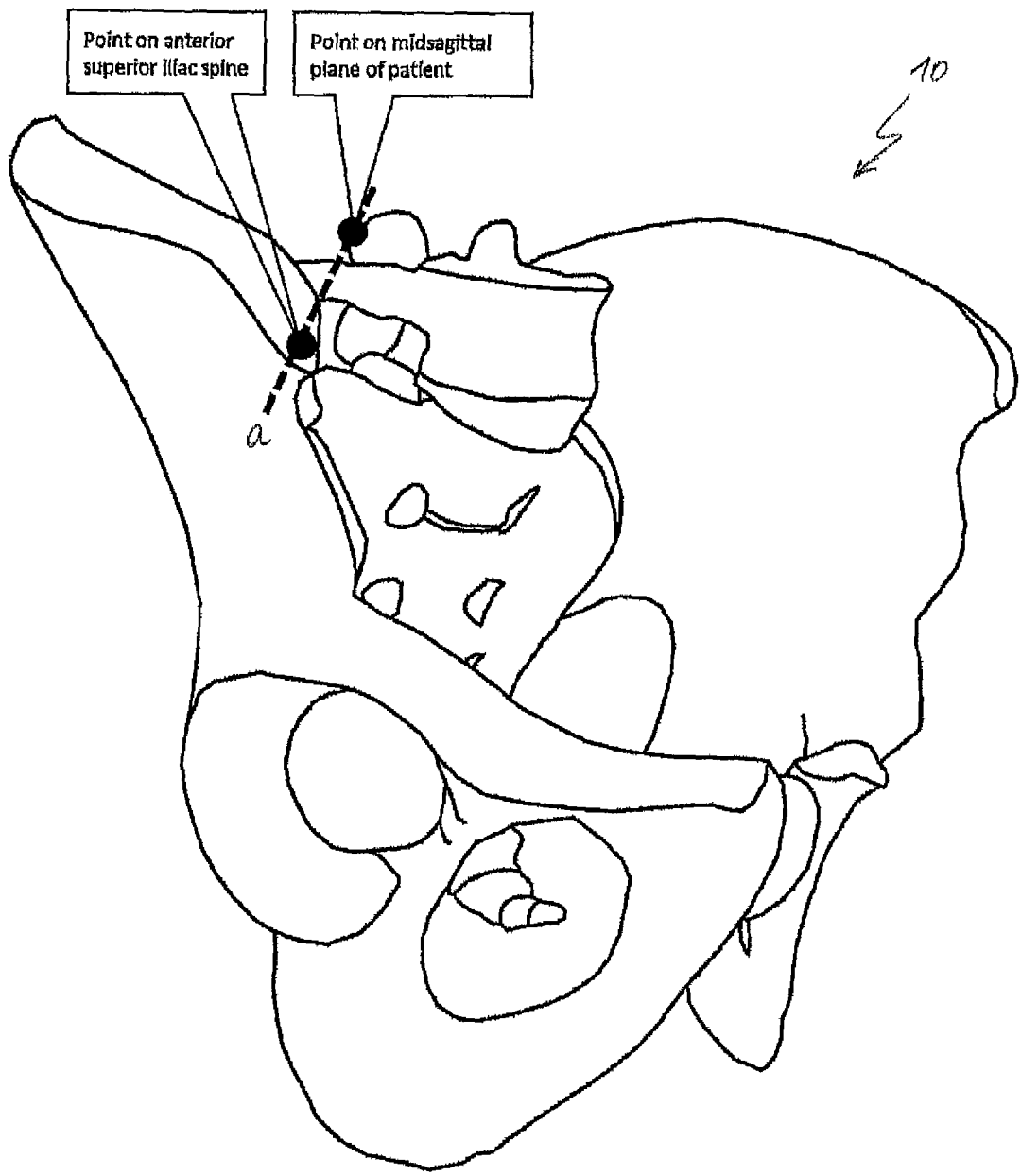
FIG. 6 shows landmarks of interest for determining characteristic axes of the pelvis.

FIG. 6 shows the positions of favoured landmarks on the pelvis 10 which are usable for conducting the above-described pelvis application. The two landmarks define a characterising axis a of the pelvis 10. The landmarks preferably are a point at the anterior superior iliac spine and a point on the midsagittal plane of the patient. These points can easily be determined without any surgical activity, in particular they can be determined tactically by e.g. manual assessment through the patient's skin.

Figure 7:
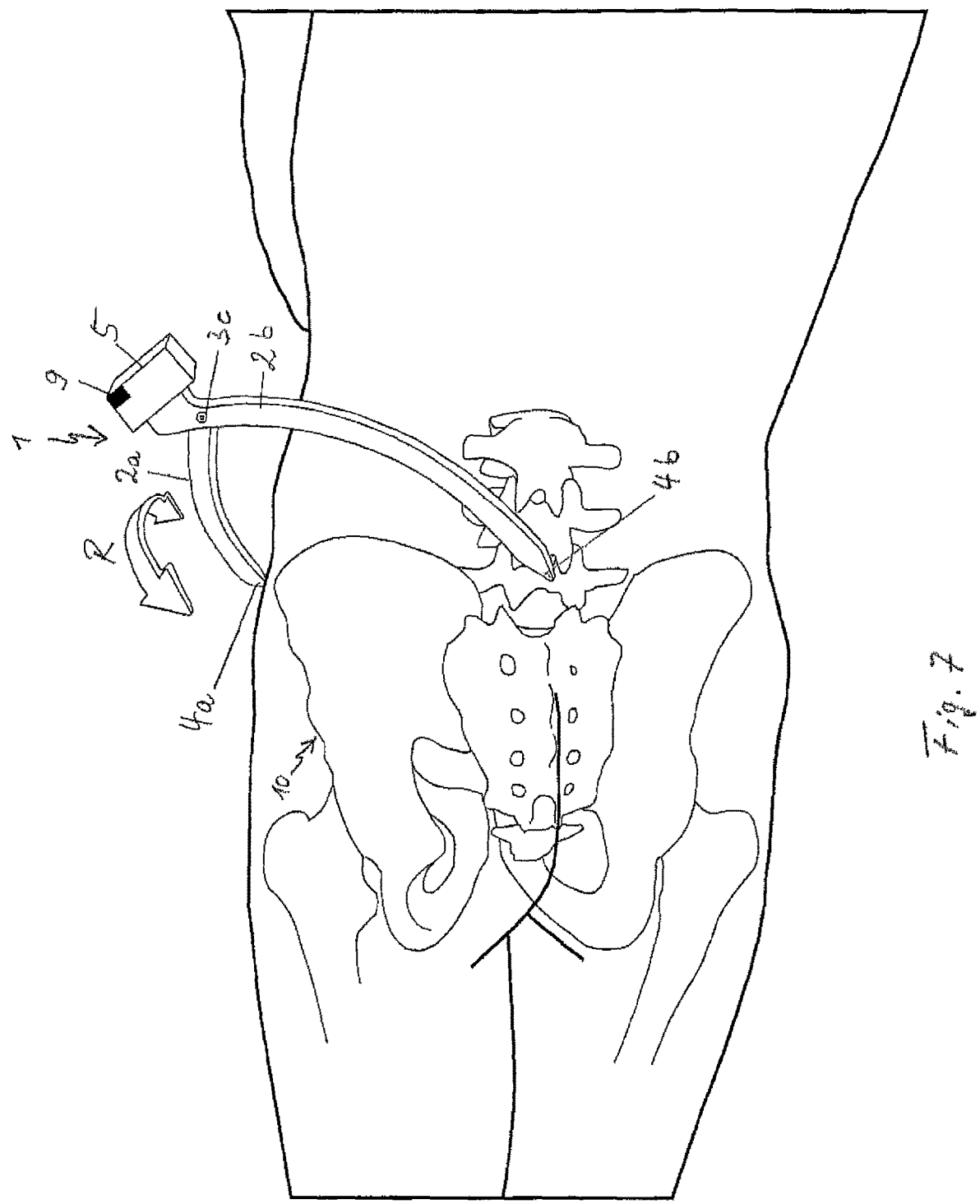
FIG. 7 shows an application of the inventive registration apparatus according to a fourth embodiment on the pelvis.

FIG. 7 gives an impression of the pelvis application in which a registration apparatus 1 according to a fourth embodiment is used. In this embodiment, the registration apparatus 1 comprises an inertial sensor 5 (and no optical sensor 6), the position of which in the global coordinate system is preferably predetermined and known. Information on a movement of the registration apparatus 1 gathered by the inertial sensor 5 is preferably transmitted from the registration apparatus 1 via a communication interface 9 to the computer of the navigation system. The pointed contacting portions 4a, 4b disposed at the ends of flanks 2a, 2b are placed on the landmarks described with reference to FIG. 6, and the registration apparatus is rotated along the trajectory R in order to determine the position and preferably the orientation of the characterising axis a defined by the positions of the respective landmarks. In particular, the orientation (in particular angular values defining the orientation) is (are) determined preferably based on the determined information about the position of the sensor 5 and/or the axis a.

LIST OF REFERENCE SIGNS 1 registration apparatus
2a, 2b flank
3 pivot portion
3a, 3b gear wheels
3c, 3d rotation centre of gear wheel
3e locking mechanism
4a, 4b contacting portion
5 inertial sensor
6 optical sensor
7 rotation mechanism
8 external reference (optical reference)
9 communication interface
10 pelvis
11 knee
a axis of rotation
e distance between landmarks
i distance between inertial sensor to mirror plane
o distance of optical sensor to mirror plane
r distance of sensor to axis a
R direction of rotation

The invention claimed is:

1. A medical registration apparatus comprising:
a pivot portion comprising a first gear wheel having a first rotation center and a second gear wheel having a second rotation center, the first and second gear wheels each having teeth configured to engage each other;
a first flank extending from the first gear wheel, the first flank and the first gear wheel being unitary, the first flank being rotatable with respect to the first rotation center;
a second flank extending from the second gear wheel, the second flank and the second gear wheel being unitary, the second flank being rotatable with respect to the second rotation center;
a first contacting portion positioned at a distal end of the first flank and a second contacting portion positioned at a distal end of the second flank, the first contacting portion and the second contacting portion being configured to be placed on an anatomical body part, a line passing through the first contacting portion and the second contacting portion defining a rotation axis about which the apparatus may rotate;
wherein the first and the second contacting portions and the first and the second rotation centers of the first and the second gear wheels lie in the same plane for every opening angle of the first and the second flanks; and
an active sensor that is configured to acquire data representing current spatial relationship information of the medical registration apparatus, the active sensor being positioned at proximal ends of the first and the second flanks with an offset to the rotation axis.

2. The registration apparatus according to claim 1, wherein the active sensor comprises an inertial sensor and/or an optical sensor.

3. The registration apparatus according to claim 1, wherein the active sensor comprises an optical sensor and an inertial sensor, the optical sensor and the inertial sensor being relatively positioned with a predetermined spatial relationship.

4. The registration apparatus according to claim 1, wherein a distance from the first contacting portion to the first rotation center is the same as a distance from the second contacting portion to the second rotation center.

5. The registration apparatus according to claim 1, wherein the first contacting portion is connected to the first flank via a joint or rotation mechanism and/or the second contact portion is connected to the second flank via a joint or rotation mechanism.

6. The registration apparatus according to claim 1, further comprising a locking mechanism located in between the flanks and fastened to each flank between the contacting portion and the pivot portion to secure the first and the second flanks in a fixed position with respect to each other.

7. A method for registering an axis of a medical registration apparatus with respect to an active sensor of the medical registration apparatus, the medical registration apparatus comprising:
a pivot portion comprising a first gear wheel having a first rotation center and a second gear wheel having a second rotation center, the first and second gear wheels each having teeth configured to engage each other;
a first flank extending from the first gear wheel, the first flank and the first gear wheel being unitary, the first flank being rotatable with respect to the first rotation center;
a second flank extending from the second gear wheel, the second flank and the second gear wheel being unitary, the second flank being rotatable with respect to the second rotation center;
a first contacting portion positioned at a distal end of the first flank and a second contacting portion positioned at a distal end of the second flank, the first contacting portion and the second contacting portion being configured to be placed on an anatomical body part, a line passing through the first contacting portion and the second contacting portion defining a rotation axis about which the apparatus may rotate;
wherein the first and the second contacting portions and the first and the second rotation centers of the first and the second gear wheels lie in the same plane for every opening angle of the first and the second flanks; and
the active sensor, which is configured to acquire data representing current spatial relationship information of the medical registration apparatus, the active sensor being positioned at proximal ends of the first and the second flanks with an offset to the rotation axis;
the method comprising:
acquiring, at a processor of a computer operably associated with the active sensor of the medical registration apparatus and from the active sensor of the medical registration apparatus, sensor movement data representing a rotational movement of the active sensor of the medical registration apparatus around the rotation axis of the medical registration apparatus;
determining, by the processor and based on the sensor movement data, axis registration data representing a spatial relationship of the rotation axis of the medical registration apparatus relative to the active sensor of the medical registration apparatus.

8. The method according to claim 7, wherein the active sensor of the medical registration apparatus comprises an optical sensor, and the method further comprises:
acquiring, at the processor from the optical sensor of the medical registration apparatus, optical sensor data representing a distance between the optical sensor of the medical registration apparatus and an external reference; and determining, by the processor based on the optical sensor data and the axis registration data, spatial axis data representing a spatial relationship of the rotation axis of the medical registration apparatus relative to the external reference.

9. The method according to claim 7, wherein the rotation axis of the medical registration apparatus is aligned with a characteristic axis of an anatomical body part.

10. A non-transitory computer-readable storage medium storing a program for registering an axis of a medical registration apparatus with respect to an active sensor of the medical registration apparatus, the medical registration apparatus comprising:
   a pivot portion comprising a first gear wheel having a first rotation center and a second gear wheel having a second rotation center, the first and second gear wheels each having teeth configured to engage each other;
   a first flank extending from the first gear wheel, the first flank and the first gear wheel being unitary, the first flank being rotatable with respect to the first rotation center;
   a second flank extending from the second gear wheel, the second flank and the second gear wheel being unitary, the second flank being rotatable with respect to the second rotation center;
   a first contacting portion positioned at a distal end of the first flank and a second contacting portion positioned at a distal end of the second flank, the first contacting portion and the second contacting portion being configured to be placed on an anatomical body part, a line passing through the first contacting portion and the second contacting portion defining a rotation axis about which the apparatus may rotate;
   wherein the first and the second contacting portions and the first and the second rotation centers of the first and the second gear wheels lie in the same plane for every opening angle of the first and the second flanks; and
   the active sensor, which is configured to acquire data representing current spatial relationship information of the medical registration apparatus, the active sensor being positioned at proximal ends of the first and the second flanks with an offset to the rotation axis;
   the program, when running on a computer operably associated with the active sensor of the medical registration apparatus or when loaded onto the computer, causes the computer to:
   acquire, from the active sensor of the medical registration apparatus, sensor movement data representing a rotational movement of the active sensor of the medical registration apparatus around the rotation axis; and
   determine, based on the sensor movement data, axis registration data representing a spatial relationship of the rotation axis of the medical registration apparatus relative to the active sensor of the medical registration apparatus.

11. The non-transitory computer-readable storage medium according to claim 10, wherein the active sensor of the medical registration apparatus comprises an optical sensor, and the program further causes the computer to:
   acquire, from the optical sensor of the medical registration apparatus, optical sensor data representing a distance between the optical sensor of the medical registration apparatus and an external reference;
   determine, based on the optical sensor data and the axis registration data, spatial axis data representing a spatial relationship of the rotation axis of the medical registration apparatus relative to the external reference.

12. A medical navigation system comprising:
   a computer comprising the non-transitory computer-readable storage medium according to claim 10; and
   a detection unit configured to detect a position of the medical registration apparatus.

13. The medical navigation system of claim 12, wherein the detection unit comprises a camera, an ultrasound receiver, or analytical device.

14. The registration apparatus of claim 6, wherein the locking mechanism comprises a ratchet or interlocking teeth.

* * * * *